United States Patent [19]

Dessau

[11] 4,309,281
[45] Jan. 5, 1982

[54] SELECTIVE SORPTION BY ZEOLITES

[75] Inventor: Ralph M. Dessau, Edison, N.J.

[73] Assignee: Mobil Oil Corporation, New York, N.Y.

[21] Appl. No.: 105,190

[22] Filed: Dec. 19, 1979

[51] Int. Cl.³ .............................................. C07C 7/13
[52] U.S. Cl. .................................. 208/310 Z; 55/75; 210/690; 585/820
[58] Field of Search .................... 208/310 Z; 585/820; 55/75; 210/690

[56] References Cited

U.S. PATENT DOCUMENTS 3,485,748  12/1969  Eberly et al. ................. 208/310 Z
3,732,326   5/1973  Chen ............................. 208/310 Z Primary Examiner—Delbert E. Gantz
Assistant Examiner—William Leader
Attorney, Agent, or Firm—Huggett Charles A.; Michael G. Gilman; Dennis P. Santini

[57] ABSTRACT

Improved hydrocarbon separation processes by the selective sorption properties of a novel class of zeolites are provided. The novel class of zeolites is characterized by a silica to alumina mole ratio greater than 12 and a constraint index within the approximate range of greater than about 2 to about 12. The separations encompassed by this invention include paraffins from aromatics, olefins from aromatics, olefins from paraffins, linear paraffins from branched paraffins, linear olefins from branched olefins, methyl branched hydrocarbons from more highly branched hydrocarbons, higher molecular weight components from lower molecular weight components within an homologous series, n-paraffins or methylparaffins from cycloparaffins, n-alkyl or methyl alkyl substituted aromatics from more highly branched isomers, mixed paraffins from aromatics (dewaxing), and non-aromatic methyl-branched hydrocarbons from aromatics. Also mono-substituted or para-disubstituted aromatics can be separated from ortho- and/or meta-disubstituted or more highly substituted aromatics. By reducing the diffusional rate characteristics of the aforesaid zeolites, improved separation of p-xylene from its isomers is also attained.

9 Claims, No Drawings

SELECTIVE SORPTION BY ZEOLITES

BACKGROUND OF THE INVENTION

1. Field of the Invention

This invention relates to adsorptive hydrocarbon separation processes using crystalline zeolites. More specifically, the claimed invention pertains to the separation of paraffins from aromatics, olefins from paraffins, olefins from aromatics, linear hydrocarbons from branched hydrocarbons, p-xylene from its isomers, n-paraffins from cycloparaffins, and separations based on molecular weight differences within an homologous series. This invention also relates to the separation of n-alkyl or methylalkyl substituted aromatics from more highly branched isomers; the separation of mixed paraffins from aromatics (dewaxing); and the separation of non-aromatic methyl-branched hydrocarbons from aromatics.

2. Description of the Prior Art

It has long been known that certain porous substances such as silica gel, activated char, and indeed zeolites, have certain selective adsorption characteristics useful in resolving a hydrocarbon mixture into its component parts. Thus, silica gel is selective in removing aromatic hydrocarbons from non-aromatic hydrocarbons and activated chars are useful in separating olefins from mixtures with paraffins. Similarly, it is well known in the separation art that certain crystalline zeolites can be used to separate certain hydrocarbons from feed mixtures.

The selective sorption properties of zeolites are generally known and have been described, for instance, in U.S. Pat. No. 2,850,549 to F. A. Ray, U.S. Pat. No. 2,866,835 to C. N. Kimberlin, Jr. et al, U.S. Pat. No. 3,037,338 to T. L. Thomas, and U.S. Pat. No. 3,218,367 to N. Y. Chen. The general sorption properties of zeolites have been disclosed in some of the earlier patents on the zeolites per se, namely U.S. Pat. No. 2,882,243 and U.S. Pat. No. 2,882,244 to R. M. Milton and other patents. Additionally, there are numerous literature references, especially those of Professor Barrer, which deal extensively with the sorption properties of crystalline zeolites. Generally speaking, crystalline zeolites are shape-selective in that they will admit compounds of designated geometry while excluding larger molecules.

The separation of normal paraffins from branched chained paraffins for example can be accomplished by using a type A zeolite which has pore openings from 3 to about 5 Angstroms. Such a separation process is disclosed in U.S. Pat. Nos. 2,985,589 and 3,201,491. These adsorbents allow a separation based on the physical size differences in the molecules by allowing the smaller or normal hydrocarbons to be passed into the cavities within the zeolitic adsorbent, while excluding the larger or branched chain molecules. U.S. Pat. Nos. 3,265,750 and 3,510,423 for example, disclose processes in which larger pore diameter zeolites such as the type X or type Y structured zeolites can be used to separate olefinic hydrocarbons from non-olefinic hydrocarbons. Processes to separate straight chain hydrocarbons from a mixture of straight chain and non-straight chain hydrocarbons using a molecular sieve selective adsorbent are described in U.S. Pat. Nos. 3,619,409 and 3,619,416.

Additionally, such crystalline zeolites will exclude aromatics such as benzene while admitting normal hexane. It has been disclosed in British Pat. No. 600,453 of Apr. 9, 1948 to R. M. Barrer that zeolites can be employed as selective sorption agents and that such zeolites will sorb polar molecules in preference to less polar molecules. A method for selectively sorbing a compound of low polarity in admixture with a compound of the same or greater polarity using a zeolite is disclosed in U.S. Pat. No. 3,732,326.

U.S. Pat. No. 3,723,302 discloses a process for separating olefins from a feed stream containing olefins and paraffins using type X or type Y zeolites. A process for the separation of olefins from a hydrocarbon feed mixture using a zeolite absorbent is disclosed in U.S. Pat. No. 3,969,223. A process for the separation and recovery of hydrocarbons selected from paraffins or olefins or both from admixture with aromatic hydrocarbons using aluminum-deficient mordenite is disclosed in U.S. Pat. No. 3,485,748.

The separation of xylene isomers has received a great deal of attention. This interest is generally attributed to the usefulness of para-xylene in the manufacture of terephthalic acid which is an intermediate in the manufacture of synthetic fibers such as "Dacron", "Mylar" and "Terylene". Mixtures of xylene isomers generally contain a concentration of about 24 weight percent para-xylene in the equilibrium mixture. Processes to separate xylene isomers include low temperature crystallization, fractional distillation, selective sulfonation with subsequent hydrolysis and selective solvent separation. Such processes, however, have involved high operation costs and usually result in a limited yield.

U.S. Pat. No. 3,868,429 discloses a method to separate xylene isomers by using activated carbon.

The separation of xylene isomers by the use of faujasite zeolites (type X and type Y zeolites) has been extensively studied. The use of type X and type Y zeolites in xylene isomer separation and similar separations is disclosed in U.S. Pat. Nos. 3,114,782; 3,126,425; 3,133,126; 3,558,730; 3,558,732; 3,626,020; 3,663,638; 3,665,046; 3,686,342; 3,943,183 and 4,051,192.

U.S. Pat. No. 3,793,385 discloses a process for the separation of aromatic isomers, more particularly the separation of xylene isomers by using zeolite beta.

The use of ZSM-5 class crystalline zeolites, i.e. silica to alumina mole ratio of at least 12 and constraint index within the range of 1 to 12, for separating $C_8$ aromatic mixtures is disclosed in U.S. Pat. No. 3,699,182.

The ZSM-5 class of crystalline zeolite has been shown to be selective. This shape selectivity can be further enhanced by the use of very large crystals, impregnation with Mg and P to reduce zeolite pore opening and coke selectivation. These modified zeolite catalysts have been very effective in such reactions as selective toluene disproportionation which yields predominantly paraxylene as the product and toluene-ethylene alkylation yielding primarily para-ethyltoluene.

Zeolite ZSM-5 possesses pore openings intermediate in size between the small pore and the large pore zeolites. It sorbs at room temperature straight chain monomethyl-substituted paraffins and monocyclic hydrocarbons at significantly faster rates than those containing dimethyl-substituted or quaternary carbon atoms, and it excludes molecules with critical dimensions larger than that of 1,3,5-trimethylbenzene. Zeolite ZSM-5 has a pore system which differentiates catalytically molecules having a straight chain, a methyl substitution and a dimethyl substitution. The catalytic properties of ZSM-5 are further elucidated by Chen and Garwood in *Some Catalytic Properties of ZSM-5, a New Shape Selec-*

*tive Zeolite*, JOURNAL OF CATALYSIS, Vol. 52, No. 3 (May 1978).

Satterfield and Cheng, *Liquid Sorption Equilibrium of Selected Binary Hydrocarbon Systems in Type Y Zeolites*, AICHE JOURNAL, Vol. 18, No. 4, p. 720, July 1972 and Satterfield and Smeets, *Liquid Sorption Equilibria of Selected Binary Paraffin Systems in NaY Zeolite*, AICHE JOURNAL, Vol. 20, No. 3, p. 618, May 1974, teach that on zeolite Y aromatic compounds are selectively adsorbed over paraffins and smaller compounds are adsorbed in preference to larger compounds. Contrary to this prior art, the instant invention yields the unexpected results of selective absorption of paraffins over aromatics and selective adsorption of higher molecular weight molecules over smaller members of the same family.

SUMMARY OF THE INVENTION

In accordance with the present invention, there have now been discovered improved hydrocarbon separation processes accomplished by the selective sorption properties of a novel class of zeolites. The novel class of zeolites useful in this invention are characterized by a silica to alumina mole ratio of at least 12 and a constraint index within the approximate range of greater than about 2 to about 12.

The hydrocarbon separation processes embraced by the instant invention include the following:

(1) the separation of paraffins from aromatics;

(2) the separation of olefins from paraffins;

(3) the separation of olefins from aromatics;

(4) the separation of linear hydrocarbons (paraffins or olefins, etc.) from branched hydrocarbons (paraffins or olefins, etc.) and methyl branched hydrocarbons from more highly branched hydrocarbons;

(5) the separation of mono-substituted or para-disubstituted aromatics from ortho- and/or meta-disubstituted or more highly substituted aromatics;

(6) the separation of n-paraffins or methyl paraffins from cycloparaffins;

(7) separations based on molecular weight (boiling point) differences within an homologous series;

(8) the separation of n-alkyl or methylalkyl substituted aromatics from more highly branched isomers;

(9) the separation of mixed paraffins from aromatics (dewaxing); and

(10) the separation of non-aromatic methyl-branched hydrocarbons from aromatics.

DESCRIPTION OF THE SPECIFIC EMBODIMENTS

The processes of this invention are concerned with the separation of hydrocarbon mixtures by the selective sorption properties of a novel class of zeolites. The novel class of zeolites is characterized by a silica to alumina mole ratio of at least 12 and a constraint index within the approximate range of greater than about 2 to about 12.

The novel class of zeolites of the instant invention possess the ability to selectively sorb linear paraffins or linear olefins (non-aromatic compounds) from aromatics, olefins from paraffins, linear hydrocarbons from branched hydrocarbons, and methyl branched hydrocarbons from more highly branched hydrocarbons. Said zeolites can also affect the selective sorption of mono-substituted or para-disubstituted aromatics from ortho- and/or meta-disubstituted or more highly substituted aromatics and higher molecular weight (boiling) hydrocarbons from lower molecular weight (boiling) hydrocarbons within an homologous series. Also n-paraffins or methyl paraffins are selectively sorbed and thus separated from cycloparaffins using this novel class of zeolites. Further, these zeolites can affect the selective sorption of n-alkyl or methylalkyl substituted aromatics from more higher branched isomers. This class of zeolites is also effective for the selective sorption of iso-paraffins from a mixture of iso-paraffins and aromatics.

Utilizing the novel class of zeolites of the present invention with crude oils, heavy oils and lube base stocks can be quite useful in the dewaxing of such oils via the selective sorption and separation of paraffins. Thus paraffins can be selectively removed to such an extent so as to reduce the pour point of the oil, i.e. increase its fluidity.

Also included in the above mentioned separation processes of the instant invention are those processes utilizing substituted hydrocarbons, i.e. heteroatom substituted compounds. Non-limiting examples of heteroatom substituents are halogens, e.g. I, Br, Cl F; sulfur groups, e.g. thiols, disulfides, thioacids, thioesters, etc; oxygen groups, e.g. alcohols, ketones, esters, acids, etc. and nitrogen groups, e.g. amines, imines, nitriles, amides, etc. Non-limiting examples of the separation processes of the present invention using substituting hydrocarbons include the following:

(1) the separation of linear and methyl branched alkyl halides, alcohols, etc. from aromatic halides, alcohols, etc.

(2) the separation of linear halides, alcohols, etc. from branched and cyclic halides, alcohols, etc.

(3) the separation of mono-substituted and para-disubstituted aromatics containing any of the above mentioned heteroatoms from ortho- and meta- disubstituted aromatics.

Some of the processes of this invention are illustrated in Table 1. Table 1 gives competitive selective sorption results for various hydrocarbon mixtures in the presence of ZSM-5, ZSM-11, ZSM-12 and Mordenite. As can be seen from Table 1, both ZSM-5 and ZSM-11 which represent the useful zeolites of the instant invention show much greater preference for the sorption of certain hydrocarbons as compared to ZSM-12 and Mordenite. The ability of a particular zeolite to selectively sorb one hydrocarbon in admixture with another is characterized by deriving the "selectivity".

TABLE 1

| | COMPETITIVE SORPTIONS USING ACID ZEOLITES | | | | |
|---|---|---|---|---|---|
| | SELECTIVITIES FOR VARIOUS SEPARATIONS | | | | |
| ZEOLITE | Paraffin Aromatic | n-Nonane p-Xylene | Olefins Aromatic | Heptene-1 Toluene | Linear Branched | n-Hexane 3-Methyl-pentane |
| HZSM—5 | | 57–200 | | 76 | | 12–21 |
| HZSM—11 | | 83–116 | | — | | 14 |
| HZSM—12 | | 0.9 | | 3.2 | | 2 |
| H—Mordenite | | | | | | |

TABLE 1-continued
COMPETITIVE SORPTIONS USING ACID ZEOLITES
SELECTIVITIES FOR VARIOUS SEPARATIONS

| ZEOLITE | Paraffin Aromatic | n-Nonane p-Xylene | Olefins Aromatic | Heptene-1 Toluene | Linear Branched | n-Hexane 3-Methyl-pentane |
|---|---|---|---|---|---|---|
| (dealum. Mordenite) | 1.5 | | — | | | 0.7 |

In adsorptive separation processes, an important factor that is used to determine the ability of a particular adsorbent to separate components of a feed mixture is the selectivity of the adsorbent for one component as compared to another component. The selectivity, as used throughout this specification, is defined as the ratio of the two components of the adsorbed or retained phase over the ratio of the same two components in the unadsorbed phase at equilibrium conditions. Selectivity is derived as follows:

$$\text{Selectivity} = S_{A,B} = \frac{(A \text{ adsorbed on zeolite})}{(B \text{ in solution})} \times \frac{(B \text{ adsorbed on zeolite})}{(A \text{ in solution})}$$

where A and B are the two components of the feed represented in volume percentages.

The equilibrium conditions as defined herein are determined when the feed is contacted with a bed of adsorbent and no change in composition results after such contacting. In other words, there is no net transfer of material occurring between the unadsorbed and adsorbed phases.

As can be seen, where the selectivity of the two components approaches unity, there is no preferential adsorption of one component by the adsorbent because the ratio of the feed to the components in the adsorbed and unabsorbed phases is equal. As the value of $S_{A,B}$ becomes less or greater than unity, there is a preferential selectivity by the adsorbent for one of the two components. When comparing a selectivity of component A over component B, an $S_{A,B}$ larger than unity indicates preferential adsorption of component A within the adsorbent, while an $S_{A,B}$ less than unity would indicate that component B is preferentially adsorbed by the adsorbent.

The novel processes of the instant invention involve contacting a hydrocarbon mixture, existing either as a gas, liquid or mixed phase with a member of the novel class of zeolites of this invention for a period of time to selectively sorb a preferred hydrocarbon within the internal pore structure of said zeolite. The components of the hydrocarbon mixtures that are not sorbed are thus carried off. The hydrocarbon sorbed is thereafter recovered from the internal pore structure of the zeolite by conventional desorbing techniques such as stripping. Although inert solvents were employed in static batch systems to carry out many of the experiments illustrating this invention, the novel processes of this invention can also be conducted in flow type (continuous) systems, e.g. continuous chromatographic type operation. In such a flow type system, a hydrocarbon mixture is passed through a bed containing a member of the novel class of zeolites of the present invention. The preferred hydrocarbon is adsorbed or retained in the bed, while the unadsorbed hydrocarbon is removed. The processes of this invention can be conducted in the presence of polar, e.g. water or alcohol, or non-polar solvents.

Thus, selective sorptions of the kind and type described herein can take place in the presence of water, i.e. in aqueous solution.

The temperature at which the novel processes of this invention are conducted is not critically important. The temperature, however, must be maintained below that required for chemical reaction to occur, e.g. below cracking temperature. The temperature should thus be maintained below about 150° C. Preferably, the processes of this invention can be conducted in the temperature range between ambient and about 150° C.

An improved process has now been discovered for the separation of xylene isomers. The improvement lies in effecting certain modifications to the novel class of zeolites of this invention. Thus the higher isomer selectivity already known for ZSM-5 and ZSM-11 can be further enhanced and thus magnifying the preference for the para-xylene isomer. The higher selectivities obtainable from this improved process will allow for simplified batch-type operation for conventional xylene separation processes, thereby improving the overall economics of existing xylene separation processes.

Obtaining the higher selectivities for the zeolites of this invention for this improved process can be accomplished by reducing the diffusional rate characteristics of these zeolites. Diffusional rate characteristics is defined as the rate of which a zeolite, or other adsorbent, sorbs a particular hydrocarbon, e.g. hexane or o-xylene. Modification of the diffusional rate characteristics may be suitably effected by precoking. Another means of achieving desired lower diffusional rate characteristics is the use of large crystal size zeolite having a minimum crystal dimension of greater than about 0.5 microns, generally in the approximate range of between about 0.5 microns and about 250 microns, and preferably in the range of between about 0.5 microns and greater than 250 microns.

As used throughout this specification and claims, zeolites with crystal diameters of about 0.02 microns to about 0.5 microns will be designated as "small crystal size" and zeolites with crystal diameters greater than about 0.5 microns will be designated as "large crystal size". Still another means of achieving desired lower diffusional rate characteristics is to incorporate bulky cations such as cesium or tetramethylammonium cations with the useful zeolites of this invention.

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred in some instances to use zeolites having much higher silica to alumina mole ratios, i.e. 1600 and above. In addition, zeolites as otherwise characterized herein but which are substantially free of aluminum, i.e. having silica to alumina mole ratios up to and including infinity, are found to be useful and even preferable in some instances. Such "high silica" or "highly siliceous" zeolites are intended to be included within this description. Also to be included in this definition are the pure silica analogs of the useful zeolites of this invention, i.e. having absolutely no aluminum (silica to alumina mole ratio of infinity). Thus zeolites useful herein have silica to alumina mole ratios of between about 13 and infinity.

The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e. 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

There also may be instances where the activity is so low (i.e. silica to alumina mole ratio approaching infinity) that the constraint index cannot be adequately measured, if at all. In such situations, Constraint Index is meant to mean the Constraint Index of the exact same substance (i.e. same crystal structure as determined by such means as x-ray diffraction pattern) but in a measureable form (i.e. aluminum containing form).

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Constraint Index (CI) values for some typical materials are:

|  | C.I. |
|---|---|
| ZSM—4 | 0.5 |
| ZSM—5 | 8.3 |
| ZSM—11 | 8.7 |
| ZSM—12 | 2 |
| ZSM—23 | 9.1 |
| ZSM—35 | 4.5 |
| ZSM—38 | 2 |
| TMA Offretite | 3.7 |
| Clinoptilolite | 3.4 |
| Beta | 0.6 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of greater than about 2 to about 12 for the Constraint Index of a particular zeolite. Such a zeolite exhibits the constrained access as herein defined and is to be regarded as having a Constraint Index in the range of greater than about 2 to about 12. Also contemplated herein as having a Constraint Index in the range of greater than about 2 to about 12 and therefore within the scope of the defined novel class of highly siliceous zeolites are those zeolites which, when tested under two or more sets of conditions within the above-specified ranges of temperature and conversion, produce a value of the Constraint Index slightly less than 2, e.g. 1.9, or somewhat greater than 12, e.g. 14 or 15, with at least one other value within the range of greater than about 2 to about 12. Thus, it should be understood that the Constraint Index value as used herein is an inclusive rather than an exclusive value. That is, a crystalline zeolite when identified by any combination of conditions within the testing definition set forth herein as having a Constraint Index in the range of greater than about 2 to 12 is intended to be included in the instant novel zeolite definition whether or not the same identical zeolite, when tested under other of the defined conditions, may give a Constraint Index value outside of the range of greater than about 2 to about 12.

The novel class of zeolites defined herein is exemplified by ZSM-5, ZSM-11, ZSM-23, ZSM-35, and other similar materials.

ZSM-5 is described in greater detail in U.S. Pat. No. 3,702,886 and No. Re. 29,948. The entire descriptions contained within those patents, particularly the X-ray diffraction pattern of therein disclosed ZSM-5, and incorporated herein by reference.

ZSM-11 is described in U.S. Pat. No. 3,709,979. That description, and in particular the X-ray diffraction pattern of said ZSM-11, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are unsuitable for use herein, possibly because the intra-crystalline free space is occupied by organic cations from the forming solution. They may be made suitable by heating in an inert atmosphere at 540° C. for one hour. If desired these zeolites may be base exchanged with suitable compounds, e.g. salts, to get desired cationic form, e.g. sodium, hydrogen, ammonium, etc. The presence of organic cations in the forming solution may not be absolutely essential to the formation of this type zeolite; however, the presence of these cations does appear to favor the formation of this special class of zeolite.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-23 and ZSM-35, with ZSM-5 being particularly preferred.

In a preferred aspect of this invention, the zeolites hereof are selected as those providing, among other things, a crystal framework density in the dry hydrogen form of not less than about 1.6 grams per cubic centimeter. It has been found that zeolites which satisfy all three of the discussed criteria are most desired for several reasons. Therefore, the preferred zeolites useful with respect to this invention are those having a Constraint Index as defined above of greater than about 2 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstoms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small mount of free space within the crystal, which might be expected to result in more stable structures. This free space, however, is important as the focus of catalytic activity.

Crystal framework densities of some typical zeolites, including some which are not within the purview of this invention are:

|  | Void Volume | Framework Density |
| --- | --- | --- |
| Ferrierite | 0.28 cc/cc | 1.76 g/cc |
| Mordenite | .28 | 1.7 |
| ZSM—5, 11 | .29 | 1.79 |
| ZSM—12 | — | 1.8 |
| ZSM—23 | — | 2.0 |
| Dachiardite | .32 | 1.72 |
| L | .32 | 1.61 |
| Clinoptilolite | .34 | 1.71 |
| Laumontite | .34 | 1.77 |
| ZSM—4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite can be conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

The following examples will serve to illustrate the process of the invention without limiting same.

EXAMPLE 1

This example illustrates the preparation of small crystal size ZSM-5.

An organic salt solution was prepared by mixing 1.6 parts of n-propyl bromide, 1.9 parts of tri-n-propylamine, 3.1 parts of methyl ethyl ketone and 10.4 parts of water. The mixture was reacted at about 100° C. for about 14 hours. The aqueous phase of the reacted mixture is designated Solution A.

A sodium silicate solution was prepared by mixing 16 parts water and 27.7 parts sodium silicate (28.7 wt % $SiO_2$, 8.9 wt % $Na_2O$, 62.4% $H_2O$) followed by addition of 0.08 parts Daxad 27 (W. R. Grace & Co., Chem. Div.) The solution was cooled to approximately 15° C.

An acid solution was prepared by adding 1 part aluminum sulfate (17.2 wt % $Al_2O_3$) to 16.4 parts water followed by 2.4 parts NaCl and 2.9 parts of Solution A.

These solutions were mixed in an agitated vessel while 3.9 parts of NaCl were added. The gel molar ratios expressed as oxides are the following.

$SiO_2/Al_2O_3 = 78.4$ $Na_2O/Al_2O_3 = 49.9$

The gel was agitated for 4 hours at ambient temperature then heated to 95°–110° C. and held for 40 hours with severe agitation. When approximately 65% of the gel was crystallized, the temperature was increased to 150°–160° C. and held there until crystallization was complete.

The zeolite slurry product was diluted with 4–5 parts water per part slurry and 0.0002 parts of flocculent (Rohm & Haas Primafloc C-7) per part slurry, allowed to settle and supernatant liquid was drawn off. The settled solids were reslurried to the original volume of the preceding step with water and 0.00005 parts of flocculent per part slurry. After settling, the aqueous phase was decanted. This procedure was repeated until the sodium level of the zeolite was less than 1.0wt %. The washed zeolite was then filtered, dried and identified as ZSM-5 having a silica/alumina mole ratio of at least 12; i.e., about 70, and a constraint index of between 1 and 12; i.e., about 8.3.

The dried zeolite product was calcined in flowing $N_2$ for 3 hours at 538° C. than ion exchanged twice with 1 N $NH_4NO_3$ solution (5 parts $NH_4NO_3$ solution/1 part zeolite) for 1 hour at ambient temperature and dried at about 120° C. to arrive at a $NH_4$-ZSM-5 zeolite.

EXAMPLE 2

The preparation of the acid form (HZSM-5) of the small crystal size $NH_4$-ZSM-5 of Example 1 was conducted via the programmed calcination of the $NH_4$-ZSM-5 of Example 1 with air in a furnace at the approximate range of 2° F./minute until a temperature of 1000° F. was obtained and maintained at 1000° F. for 5 hours.

EXAMPLE 3

This example illustrates the preparation of large crystal size ZSM-5.

A sodium silicate solution was prepared by mixing 16 parts water and 27.7 parts sodium silicate (28.7 wt % $SiO_2$, 8.9 wt % $Na_2O$, 62.4% $H_2O$) followed by addition of 0.08 parts Daxad 27 (W. R. Grace Chem. Co.) The solution was cooled to approximately 15° C.

An acid solution was prepared by adding 1 part aluminum sulfate (17.2 wt % $Al_2O_3$) to 16.4 parts water followed by 2.4 parts sulfuric acid (93 wt % $H_2SO_4$) and 1.2 parts NaCl.

These solutions were mixed in an agitated vessel while 3.9 parts of NaCl were added. The gel molar ratios expressed as oxides are the following:

$SiO_2/Al_2O_3 = 78.4$ $Na_2O/Al_2O_3 = 49.9$

An organic solution was prepared by adding 1.6 parts n-propyl bromide and 3.1 parts methyl ethyl ketone to 1.9 parts tri-n-propylamine and added to the gel.

The mixture was reacted at 150°–160° F. with severe agitation for 29 hours.

The zeolite slurry product was diluted with 4–5 parts water per part slurry and 0.002 parts of flocculent (Rohm & Haas Primafloc C-7) per part slurry, allowed to settle and supernatant liquid was drawn off. The settled solids were reslurried to the original volume of the preceding step with water and 0.0005 parts of flocculent per part slurry. After settling, the aqueous phase was decanted. This procedure was repeated until the decant supernatant liquid was Cl-free. The washed zeolite was then filtered, dried and identified as ZSM-5 having a silica/alumina mole ratio of at least 12; i.e., about 70, and a constraint index of between 1 and 12; i.e., about 8.3.

The dried zeolite product was calcined in flowing $N_2$ for 3 hours at 538° C. then ion exchanged twice with 1 N $NH_4NO_3$ solution (5 parts $NH_4NO_3$ soln/1 part zeolite) for 1 hour at ambient temp. and dried at about 120° C. to arrive at a $NH_4$-ZSM-5 zeolite.

EXAMPLE 4

The preparation of the acid form (HZSM-5) of the large crystal size $NH_4$-ZSM-5 of Example 3 was conducted via the programmed calcination of $NH_4$-ZSM-5 of Example 3 with air in a furnace at the rate of about 2° F./minute until a temperature of 1000° F. was attained and maintained at 1000° F. for 5 hours.

EXAMPLE 5

This example illustrates the preparation of small crystal size ZSM-11.

A sodium silicate solution was prepared by mixing 16.8 parts water, 28.9 parts sodium silicate (28.7 wt % $SiO_2$, 8.9 wt % $Na_2O$, 62.4 wt % $H_2O$) 0.05 parts 50% wt NaOH and 0.08 parts Daxad 27 (W. R. Grace Chem. Co.).

An acid solution was prepared by adding 1 part aluminum sulfate (17.2% wt $Al_2O_3$) to 12.6 parts $H_2O$ and then adding 2.9 parts $H_2SO_4$ and 1.7 parts NaCl.

These solutions were mixed in an agitated vessel and 1.2 parts NaCl and 0.8 parts $H_2O$ were added to the gel.

An organic solution containing 2.9 parts tetrabutylammonium bromide and 4.2 parts water was then added to the gel and thoroughly blended.

The mixture was heated to 200° F. and held for 234 hours with a high level of agitation. At the end of this period the temperature was raised to 280° F. for 72 hours to complete crystallization.

The crystallized product was washed and dried and then identified as 105% crystallinity ZSM-11 by X-ray diffraction with the following chemical analysis:

|  | % wt. |
|---|---|
| $Al_2O_3$ | 1.99 |
| $SiO_2$ | 92.0 |
| Na | 0.60 |
| N | 0.65 |
| C | 9.95 |

The washed and dried zeolite product was calcined in flowing $N_2$ for 3 hours at 1000° F. then ion exchanged with 1 N $NH_4NO_3$ solution (5 parts $NH_4NO_3$ soln/1 part zeolite) for 1 hour at ambient temperature and dried at about 250° F.

The silica to alumina mole ratio of the resultant zeolite was 78.

EXAMPLE 6

This example illustrates the preparation of small crystal size zeolite $NH_4$-ZSM-12.

A reaction mixture was prepared by mixing 65 parts of Hi-Sil (a precipitated $SiO_2$), 6.3 parts NaOH, 1 part $Al(NO_3)_3$ $9H_2O$, 40 parts tetraethylammonium bromide and 310 parts $H_2O$. The mixture was charged to a vessel, thoroughly agitated and heated to about 320° F. and held for about 16 hours with agitation. At this point the reaction mixture was cooled and 1.1 parts of $NaAlO_2$ and 2.7 parts $H_2O$ were added. The reaction mixture was reheated to 320° F. and held for an additional 24 hours at 320° F. with agitation to complete crystallization.

The crystallized product was washed and dried and then identified as 90% ZSM-12 by X-ray diffraction with the following chemical analysis:

|  | % wt |
|---|---|
| $Al_2O_3$ | 1.79 |
| $SiO_2$ | 95.1 |
| Na | 0.34 |
| N | 0.98 |
| C | 7.63 |

The washed and dried zeolite was calcined in flowing $N_2$ for 3 hours at 1000° F. then ion exchanged three times with 1 N $NH_4NO_3$ solution (5 parts $NH_4NO_3$ soln/1 part zeolite) for 1 hour at ambient temperature and dried at about 250° F. to finally obtain a $NH_4$-ZSM-12 zeolite.

The silica to alumina mole ratio of the resultant zeolite was 95.

EXAMPLE 7

The preparation of HZSM-12 from the $NH_4$-ZSM-12 of Example 6 was conducted via the programmed calcination of $NH_4$-ZSM-12 with air in a furnace at the rate of about 2° F./minute until a temperature of 1000° F. was attained and maintained at 1000° F. for 5 hours.

EXAMPLE 8

Small crystal size CS-ZSM-5 was prepared by the ion-exchange of $NH_4$-ZSM-5 of Example 1 with a cesium chloride solution containing a small amount of cesium hydroxide, resulting in an ammonium removal of approximately 99%.

EXAMPLE 9

This example illustrates the preparation of a highly siliceous ZSM-5 zeolite with a silica to alumina mole ratio of about 1600 to 1.

PREREACTED ORGANICS PREPARATION

The following materials were charged to an autoclave: 0.30 parts methylethyl ketone, 0.18 parts tri-n-propylamine and 0.15 parts n-propyl bromide. The contents were mixed with gentle agitation for 15 minutes. The agitation was stopped and 1 part water was charged to the autoclave. The autoclave was sealed and heated to 220° F. and held at 220° F. for 15 hours. After this reaction period the temperature was raised to 320° F. and the unreacted organics were flashed off. The aqueous phase was removed containing the prereacted organics and contained 1.44% wt. nitrogen.

Zeolite Synthesis

Solution Preparation

Silicate Solution 1 part Q-brand sodium silicate
0.58 parts $H_2O$
0.0029 parts Daxad 27

Acid Solution 0.10 parts $H_2SO_4$
0.045 parts NaCl
0.56 parts prereacted organics
0.16 parts $H_2O$

Additional Solids 0.14 parts NaCl

Additional Liquid 0.029 parts H₂O

Procedure

The silicate solution and acid solution were mixed in a mixing nozzle to form a gel which was discharged into an autoclave to which 0.029 parts water had been previously added. The gel was whipped by agitation and 0.14 parts NaCl were added and thoroughly blended. The autoclave was sealed and heated to ~220° F. with agitation at 90 rpm and held for 54.3 hours until crystallization was complete. The contents of the autoclave were cooled and discharged. The crystallized product was analyzed by x-ray diffraction and was found to be 100% wt ZSM-5. The chemical analysis of the thoroughly washed crystalline product was as follows:

|        | % wt  | Mole Ratio |
|--------|-------|------------|
| Al₂O₃  | 0.10  | 1.0        |
| SiO₂   | 98.3  | 1670       |
| Na     | 1.6   | —          |
| Na₂O   | —     | 35.5       |
| N      | 0.75  | 63.9       |
| C      | 8.98  | 892        |

EXAMPLES 10 TO 25

Due to the high hydrophobicity of all zeolites used, no pretreatment to remove sorbed water was required prior to their use in the sorption experiments.

In order to develop a meaningful diagnostic evaluation of zeolites that could be used for predicting separation properties, the selective sorption properties of various zeolites under competitive conditions were examined. In general, two or more substrates were dissolved in an inert (non-sorbable) solvent and the relative decrease in concentration of each sorbate due to addition of various zeolites was measured.

The sorbates used were purest forms available commercially. The three inert non-sorbable solvents used were:

1,3,5-trimethylbenzene (mesitylene) from Aldrich, hereinafter designated as M
1,3,5-triisopropylbenzene from Chem Samples, hereinafter designated as T
1,3-di(trifluoromethyl)benzene from PCR Research Chem, hereinafter designated as D.

In a typical experiment, 2 grams of a solution containing two sorbates (2.5% by weight each) in an inert solvent was added directly to 1 gram of a zeolite contained in a vial. This mixture, which occasionally was shaken or stirred at room temperature, was sampled periodically for changes in substrate concentrations. These samples were analyzed by vapor phase chromatography and were compared to the original solution analyzed in the identical manner. The selectivity was calculated by the formula defined herein.

Examples 10 to 25 serve to illustrate the selective separation of a paraffin (n-hexane) from an aromatic (para-xylene).

In each of Examples 10 to 12, the zeolite employed was prepared by the general procedure of Example 2. The zeolites of Examples 13 and 14 were prepared by the general procedure of Example 1. In each of Examples 15 to 17, the zeolites utilized were prepared according to the procedure of Example 8. Examples 18 to 20 employed the zeolite prepared by the general procedure given in Example 5. The zeolites of Examples 21 and 22 were prepared in accordance with Example 7. Example 23 employed a zeolite prepared by the procedure of Example 6. In Examples 24 and 25, the zeolite employed was H-Mordenite (de-aluminized H-Zeolon) having a SiO₂/Al₂O₃ ratio of about 61.

The aforementioned zeolites were used according to the typical experiment given herein. The results of Examples 10 to 25, which are summarized in Table 2, clearly demonstrate the superior selectivity of HZSM-5 and HZSM-11 for the sorption of paraffins over aromatics. This selectivity, which occurs preferentially at room temperature in the liquid phase, is not due to kinetic diffusional causes, as both substrates readily diffuse into the zeolite. As shown in Table 2, there is an extremely high preference of both HZSM-5 and HZSM-11 for linear paraffin n-nonane relative to the aromatic para-xylene, despite the fact that the sorption capacity for each compound if taken individually would be similar.

Although the Cs and NH₄ forms of ZSM-5 and ZSM-11 are not as selective as the hydrogen forms for the separation of non-aromatic linear compounds from aromatic compounds, these cation forms still exhibited better selectivity than ZSM-12 and Mordenite.

EXAMPLES 26 TO 29

These examples show the selective sorption of an olefin (heptene-1) over an aromatic (toluene).

In each of Examples 26 and 27, the zeolite employed was prepared by the general procedure of Example 2. The zeolites of Examples 28 and 29 were prepared by the general procedure of Example 7.

The aforementioned zeolites were used in conjunction with the typical experiment given in Examples 10 to 25. The results of Examples 26 to 29 clearly demonstrate the outstanding efficacy in the use of HZSM-5 to preferentially sorb an olefin over an aromatic. The results of Examples 26 to 29 are outlined in Table 3.

EXAMPLES 30 TO 36

Examples 30 to 36 are directed to the preferential sorption of a linear paraffin over a branched (non-linear) paraffin. The linear paraffin in these examples is n-hexane and the branched paraffin is 3-methylpentane.

In Examples 30 and 31, the zeolite employed was prepared by the general procedure of Example 2.

In Example 32, the zeolite utilized was prepared by the general procedure of Example 4. The zeolite employed in Example 33 was prepared in accordance with the procedure of Example 5. In Example 34, the zeolite used was prepared according to the procedure of Example 6. The zeolite of Example 35 was prepared according to the procedure of Example 7, and the zeolite of Example 36 was H-Mordenite (de-aluminized H-Zeolon) with a SiO₂/Al₂O₃ ratio of about 61.

Following the typical experiment given in Examples 10 to 25 using the zeolites given above, Examples 30 to 36 were carried out. As shown in Table 4, linear n-hexane is selectively sorbed over non-linear 3-methylpentane by HZSM-5 and HZSM-11, in constrast to the lower selectivities exhibited by HZSM-12 and Mordenite.

If one were to compare the selective sorption of n-hexane relative to 3-methylpentane under the competitive equilibrium, non-kinetic conditions carried out herein, and examine the sorption properties of each hydrocarbon individually over a particular zeolite, the results would be very illuminating.

If these hydrocarbons are individually examined for sorption characteristics, the sorption capacity for n-hexane is almost twice that of 3-methylpentane at room temperature; at higher temperatures and consequently lower pore fillings ($\leq 60$ mg/gram), both isomers appear to sorb to a similar extent. The competitive results, on the other hand, demonstrate selectivity factors greater than 10 in favor of n-hexane (see Table 4), even at partial pore fillings.

EXAMPLES 37 TO 39

These examples illustrate the preferential sorption of a linear olefin (heptene-1) over a branched olefin (4,4-dimethyl-1-pentene) by the use of ZSM-5 and modifications thereto.

In Example 37, the zeolite utilized was prepared by the general procedure of Example 2. The zeolites used in Examples 38 and 39 were prepared by the general procedure of Example 8. These above-mentioned zeolites were used in the typical experiment given in Examples 10 to 25 and the results are summarized in Table 5. As clearly shown in Table 5, the use of cations such as cesium enhance the selective preference for linear hydrocarbons.

EXAMPLES 40 TO 42

Examples 40 to 42 serve to illustrate the use of acidic ZSM-5 in preferentially sorbing the heavier hydrocarbon over the lighter hydrocarbon within an homologous series. The preparation of HZSM-5 is given in Example 2. The results of Examples 40 to 42, carried out in accordance with the typical experiment given in Examples 10 to 25 are shown in Table 6. Such results are not unexpected in the gas phase, but also occur in the liquid phase. The applicability of this preferential sorption occurs for aromatics as well as for linear non-aromatics. Thus toluene is sorbed more readily than benzene, despite the fact that benzene has the higher melting point (a property once originally believed to be most closely related to the crystal packing efficiency of a substrate).

EXAMPLE 43

The separation of an olefin (heptene-1) from a paraffin (n-heptane) is given in this example. Zeolite HZSM-5 as prepared in accordance with the general procedure of Example 2 was used to preferentially sorb the olefin over the paraffin.

The typical experiment procedure given in Examples 10 to 25 was followed using the inert solvent M for a time of 18 hours, with 100% of the heptene-1 being sorbed and 11% of the heptane being sorbed. The total sorbed was 110 mg/g and the selectivity A/B was calculated to be infinity.

EXAMPLES 44 TO 54

Examples 44 to 54 are directed towards the separation of xylene isomers. In these examples, para-xylene was separated from ortho-xylene.

In Examples 44 to 47, the HZSM-5 was prepared as per the general procedure of Example 2. The zeolite used in Examples 48 to 50 was prepared by the general procedure of Example 8. The zeolite employed in Example 51 was derived in accordance with Example 4. In Example 51, the zeolite was prepared in accordance with Example 7, and in Examples 53 and 54 the zeolite was H-Mordenite (de-aluminized H-Zeolon) with a $SiO_2/Al_2O_3$ ratio of about 61.

In each of Examples 44 to 47, the typical experiment given in Examples 10 to 25 was carried out with the above mentioned zeolites. These examples, as shown in Table 7, demonstrate that, by taking advantage of kinetic rather than equilibrium conditions, a dramatic selectivity can be obtained for xylene isomer sorptions by the use of large crystal zeolites and by certain cation modifications.

The use of Cs-ZSM-5B (cation modification) and the use of large crystal size ZSM-5 are much more selective for the sorption of para-xylene than small crystal size unmodified ZSM-5. Thus an improved process of xylene isomer separations has now been discovered.

EXAMPLE 55

This example demonstrates the selective sorption of n-alkyl or methylalkyl substituted aromatics from more highly branched isomers.

An equimolar mixture of linear n-pentylbenzene, 1-methylbutylbenzene and 1-ethylpropylbenzene was dissolved in an inert solvent, namely, 1,3,5-triisopropylbenzene and to said mixture was added HZSM-5 prepared according to the general procedure of Example 2. The results for this example were as follows:

n-pentylbenzene sorbed: 90%
1-methylbutylbenzene sorbed: 15%
Selectivity for n-pentylbenzene over 1-methylbutylbenzene: 50
1-ethylpropylbenzene sorbed: nil From the foregoing it is apparent that the linear alkyl substituted aromatic (n-pentylbenzene) was sorbed preferentially over its branched isomers, e.g. 1-ethylpropylbenzene.

EXAMPLE 56

This example is a further demonstration of selective separations involving aromatic isomers. According to the general procedure of Examples 10–25, a mixture of 2-methylnaphthalene and 1-methylnapthalene was placed in contact with HZSM-5, prepared according to Example 2. The 2-methylnaphthalene was selectively sorbed over the 1-methylnaphthalene.

EXAMPLE 57

An oil was placed in contact with HZSM-5, prepared according to the general procedure of Example 2. Following the experimental procedure of Examples 10–25, n-paraffins $n\text{-}C_{17}$ and $n\text{-}C_{18}$ were selectively sorbed from isoparaffins, namely, isoprenoids phytane and pristane. The selectivity factor was 5 in favor of the n-paraffins.

EXAMPLE 58

This example establishes the selective sorption of mixed paraffins from aromatics. The utility of this example is that a novel dewaxing process is now available via the selective sorption of paraffins from oils.

An Arab Light Distillate (400°–650° F.) was passed over 9 g. of a highly siliceous ZSM-5 zeolite (SiO$_2$/Al$_2$O$_3$ 1600) at 250° C. in a column. Said zeolite was prepared in accordance with the general procedure of Example 9. The early fraction elutriating from the column was highly enriched in aromatics; the aromatic content increased 87.5% (based on proton n.m.r.) and the freezing point was reduced from −20° C. to −90° C.

EXAMPLE 59

The selective sorption of methyl substituted hydrocarbons vs. aromatics is clearly shown in this example.

A solution was prepared containing the following materials:

0.2 g: 2-methylheptane
0.2 g: p-xylene
0.3 g: 1-3 di(trifluoromethyl)benzene (as internal standard)
7.3 g: 1,3,5-triisopropylbenzene (inert solvent)

3 g. of the above solution was added to 1 g. of HZSM-5 prepared according to the general procedure of Example 2. At equilibrium, 63.5% of the 2-methylheptane was sorbed, whereas only 20.6% of the p-xylene was sorbed—a selectivity factor of 6.7.

EXAMPLES 60–64

In these examples, the selective separation of n-paraffins or methyl substituted paraffins from cycloparaffins was demonstrated. In each of these examples, the typical experiment given in Examples 10 to 25 was followed and the zeolite utilized for these examples was HZSM-5 prepared according to the general procedure of Example 2. The results for Examples 60–64 are given in Table 8.

EXAMPLES 65–67

In these examples, selective separations involving heteroatom substituted compounds were demonstrated. For each of these examples, the typical experimental procedure given in Examples 10–25 was followed and the zeolite utilized for all these examples was HZSM-5 prepared according to the general procedure of Example 2. The results for Examples 65–67 are given in Table 9.

EXAMPLE 68

Selective sorption of organic compounds from aqueous solution was demonstrated in this example. 2 g of an aqueous solution containing 3% by weight of each n-butyl alcohol, iso-butyl alcohol and tert-butyl alcohol was added to 1 g of HZSM-5, prepared according to the general procedure of Example 9. After several hours, virtually no tert-butyl alcohol was sorbed, only 17.3% of the iso-butyl alcohol was sorbed, whereas 90.7% of the n-butyl alcohol was sorbed.

TABLE 2

SELECTIVE SORPTION OF A PARAFFIN OVER AN AROMATIC

| Ex. No. | Zeolite | Time hrs. | Inert Solvent | n-Paraffin A | Aromatic B | % A Sorbed | % B Sorbed | Total Sorbed mg/g | Selectivity A/B |
|---|---|---|---|---|---|---|---|---|---|
| 10 | HZSM—5 | 1 | M | n-nonane | p-xylene | 98 | 17 | 55 | >200 |
| 11 | HZSM—5 | 4 | T | " | " | 72 | 3 | 56 | 82 |
| 12 | HZSM—5 | 27 | T | " | " | 74 | 4.7 | 59 | 57 |
| 13 | NH$_4$—ZSM—5 | 4 | T | " | " | 81 | 33 | 64 | 9 |
| 14 | NH$_4$—ZSM—5 | 48 | T | " | " | 84 | 32 | 65 | 11 |
| 15 | Cs—ZSM—5 | 2 | T | " | " | 89 | 52 | 65 | 8 |
| 16 | Cs—ZSM—5 | 21 | T | " | " | 91 | 52 | 66 | 9 |
| 17 | Cs—ZSM—5 | 48 | T | " | " | 91 | 52 | 66 | 9 |
| 18 | HZSM—11 | 6 | T | " | " | 98 | 34 | 66 | 99 |
| 19 | HZSM—11 | 5 | T | " | " | 77 | 3 | 60 | 116 |
| 20 | HZSM—11 | 24 | T | " | " | 78 | 4 | 61 | 83 |
| 21 | HZSM—12 | 4 | T | " | " | 27 | 30 | 43 | 0.87 |
| 22 | HZSM—12 | 24 | T | " | " | 29 | 31 | 45 | 0.90 |
| 23 | NH$_4$—ZSM—12 | 2 | T | " | " | 47 | 40 | 35 | 1.3 |
| 24 | Dealum. H—Zeolon | 1 | T | " | " | 46 | 42 | 22 | 1.2 |
| 25 | Dealum. H—Zeolon | 70 | T | " | " | 64 | 50 | 29 | 1.8 |

TABLE 3

SELECTIVE SORPTION OF AN OLEFIN OVER AN AROMATIC

| Ex. No. | Zeolite | Time hrs. | Inert Solvent | A Olefin | B Aromatic | % A Sorbed | % B Sorbed | Total Sorbed mg/g | Selectivity A/B |
|---|---|---|---|---|---|---|---|---|---|
| 26 | HZSM—5 | 0.7 | T | heptene-1 | toluene | 79 | 26 | 158 | 11 |
| 27 | HZSM—5 | 17 | T | " | " | 96 | 23 | 179 | 76 |
| 28 | HZSM—12 | 0.7 | T | " | " | 36 | 26 | 62 | 1.6 |
| 29 | HZSM—12 | 20 | T | " | " | 46 | 21 | 67 | 3.2 |

TABLE 4

SELECTIVE SORPTION OF A LINEAR PARAFFIN OVER A BRANCHED PARAFFIN

| Ex. No. | Zeolite | Time hrs. | Inert Solvent | A Linear n-Hexane | B Branched 3-Methyl-pentane | % A Sorbed | % B Sorbed | Total Sorbed mg/g | Selectivity A/B |
|---|---|---|---|---|---|---|---|---|---|
| 30 | HZSM—5 (a) | 3 | M | n-$C_6$ | 3-Me$C_5$ | 83 | 19 | 48 | 21 |
| 31 | HZSM—5 (a) | 17 | M | n-$C_6$ | 3-Me$C_5$ | 84 | 24 | 51 | 17 |
| 32 | HZSM—5 (b) | .1 | M | n-$C_6$ | 3-Me$C_5$ | 85 | 32 | 56 | 12 |
| 33 | HZSM—11 | 1 | T | n-$C_6$ | 3-Me$C_5$ | 88 | 35 | 62 | 14 |
| 34 | $NH_4$—ZSM—12 | 2 | T | n-$C_6$ | 3-Me$C_5$ | 49 | 26 | 30 | 2.7 |
| 35 | HZSM—12 | 1 | T | n-$C_6$ | 3-Me$C_5$ | 57 | 39 | 48 | 2.1 |
| 36 | Dealum. H—Zeolon | 1 | T | n-$C_6$ | 3-Me$C_5$ | 42 | 52 | 24 | 0.7 |

(a) small crystal size
(b) large crystal size

TABLE 5

SELECTIVE SORPTION OF A LINEAR OLEFIN OVER A BRANCHED OLEFIN

| Ex. No. | Zeolite | Time hrs. | Inert Solvent | A Linear Olefin | B Branched Olefins | % A Sorbed | % B Sorbed | Total Sorbed mg/g | Selectivity A/B |
|---|---|---|---|---|---|---|---|---|---|
| 37 | HZSM—5 | 18 | M | heptene-1 | 4,4-dimethyl-pentene-1 | 69 | 30* | 95 | 5.3 |
| 38 | Cs—ZSM—5 | 0.2 | M | " | 4,4-dimethyl-pentene-1 | 52 | 5 | 60 | 20 |
| 39 | Cs—ZSM—5 | 72 | M | " | 4,4-dimethyl-pentene- | 50 | 11 | 64 | 8 |

*Extensive isomerization of both olefins occurred.

TABLE 6

SELECTIVE SORPTION BASED ON MOLECULAR WEIGHT DIFFERENCES WITHIN A HOMOLOGOUS SERIES

| Ex. No. | Zeolite | Time hrs. | Inert Solvent | A Heavier Hydrocarbon | B Lighter Hydrocarbon | % A Sorbed | % B Sorbed | Total Sorbed mg/g | Selectivity A/B |
|---|---|---|---|---|---|---|---|---|---|
| 40 | HZSM—5 | 2 | M | n-nonane | n-hexane | 82 | 56 | 66 | 3.5 |
| 41 | HZSM—5 | 2 | M | n-hexadecane | n-nonane | 74 | 33 | 71 | 5.7 |
| 42 | HZSM—5 | 2 | M | toluene | benzene | 83 | 68 | 72 | 2.3 |

TABLE 7

SELECTIVE SORPTION OF PARA-XYLENE FROM ITS ISOMERS

| Ex. No. | Zeolite | Time hrs. | Inert Solvent | A | B | % A Sorbed | % B Sorbed | Total Sorbed mg/g | Selectivity A/B |
|---|---|---|---|---|---|---|---|---|---|
| 44 | HZSM—5 (a) | 1 | M | p-Xylene | o-Xylene | 84 | 11 | 42 | 43 |
| 45 | HZSM—5 (a) | 24 | M | " | " | 63 | 25 | 42 | 5.1 |
| 46 | HZSM—5 (a) | 96 | M | " | " | 68 | 28 | 45 | 5.3 |
| 47 | HZSM—5 (a) | 0.1 | D | " | " | 86 | 8 | 56 | 71 |
| 48 | Cs—ZSM—5 (a) | 0.5 | M | " | " | 96 | 4 | 40 | >500 |
| 49 | Cs—ZSM—5 (a) | 0.1 | D | " | " | 98 | 10 | 51 | approx. 400 |
| 50 | Cs—ZSM (a) | 24 | D | " | " | 89 | 20 | 52 | 31 |
| 51 | HZSM—5 (b) | 120 | M | " | " | 94 | 8 | 48 | >200 |
| 52 | $NH_4$ZSM—12 | 2 | T | " | " | 57 | 19 | 36 | 5.5 |
| 53 | Dealum. H—Zeolon | 0.5 | T | " | " | 34 | 31 | 15 | 1.16 |
| 54 | Dealum. H—Zeolon | 70 | T | " | " | 65 | 63 | 29 | 1.06 |

(a) small crystal size
(b) large crystal size

TABLE 8

SELECTIVE SORPTION OF n-PARAFFINS OVER CYCLOPARAFFINS

| Ex. No. | A Paraffin | B Cycloparaffin | % A Sorbed | % B Sorbed | Selectivity A/B |
|---|---|---|---|---|---|
| 60 | n-decane | cis, trans-decalin | (only decane sorbed) | | |
| 61 | n-hexane | cyclohexane | 75.0 | 4.9 | 58 |
| 62 | n-heptane | cycloheptane | 76.6 | 7.6 | 40 |
| 63 | n-octane | cyclooctane | 61.4 | 0 | infinity |
| 64 | 3-methyl- | cyclohexane | 36.5 | 12.4 | 4 |

TABLE 8-continued
SELECTIVE SORPTION OF n-PARAFFINS OVER CYCLOPARAFFINS

| Ex. No. | A Paraffin | B Cycloparaffin | % A Sorbed | % B Sorbed | Selectivity A/B |
|---|---|---|---|---|---|
| | pentane | | | | |

TABLE 9

| Example No. | Compound A | Compound B | % A Sorbed | % B Sorbed | Selectivity A/B |
|---|---|---|---|---|---|
| 65 | 1-chloroheptane (paraffinic) | chlorobenzene (aromatic) | 76.1 | 2.5 | 7100 |
| 66 | n-butylacetate (linear) | iso-butylacetate (branched) | 86.4 | 14.0 | 39 |
| 67 | P-cresol (para) | O-cresol (ortho) | 73.0 | 48.9 | 3 |

What is claimed is:

1. A process for the selective separation of a non-aromatic compound in admixture with an aromatic compound, said compounds selected from the group consisting of hydrocarbons and substituted hydrocarbons, which comprises contacting the mixture with zeolite ZSM-11, said zeolite characterized by a silica to alumina mole ratio of at least about 12, to effect the selective sorption of said non-aromatic compound by said zeolite.

2. The process of claim 1 wherein said zeolite is calcined in an inert atmosphere at a temperature of from about 538° C. to about 593° C. for from about 1 hour to about 5 hours.

3. The process of claim 1 wherein said zeolite has its original cations replaced, at least in part, by ion exchange with a cation selected from the group consisting of hydrogen, ammonium, rare earth metals and metals from Groups I through VIII of the Periodic Table of Elements.

4. The process of claim 2 wherein said calcined zeolite has its original cations replaced, at least in part, by ion exchange with a cation selected from the group consisting of hydrogen, ammonium, rare earth metals and metals from Groups I through VIII of the Periodic Table of Elements.

5. The process of claim 3 wherein said ion exchanged zeolite is calcined in an inert atmosphere at a temperature of from about 538° C. to about 593° C. for from about 1 hour to about 5 hours.

6. The process of claim 1 wherein said non-aromatic compound is a paraffin.

7. The process of claim 6 wherein said paraffin is n-nonane and said aromatic compound is p-xylene.

8. The process of claim 1 wherein said process occurs in a batch system.

9. The process of claim 1 wherein said process occurs in a continuous system.

* * * * *

UNITED STATES PATENT AND TRADEMARK OFFICE
CERTIFICATE OF CORRECTION

PATENT NO. : 4,309,281
DATED : January 5, 1982
INVENTOR(S) : Ralph M. Dessau

It is certified that error appears in the above-identified patent and that said Letters Patent are hereby corrected as shown below:

Column 14, line 6      "% wt" should be the heading for column 2

Columns 21 and 22
Table 7, Ex. No. 50      "Cs-ZSM(a)" should read --Cs-ZSM-5(a)--

Signed and Sealed this

Thirteenth Day of April 1982

[SEAL]

Attest:

GERALD J. MOSSINGHOFF

*Attesting Officer*      *Commissioner of Patents and Trademarks*